US009861592B2

(12) United States Patent
Liu et al.

(10) Patent No.: US 9,861,592 B2
(45) Date of Patent: Jan. 9, 2018

(54) METHODS AND COMPOSITIONS FOR TREATING NEURODEGENERATIVE DISEASES

(71) Applicant: Golden Biotechnology Corporation, Jersey City, NJ (US)

(72) Inventors: Sheng-Yung Liu, New Taipei (TW); Wu-Che Wen, New Taipei (TW); Chih-Ming Chen, New Taipei (TW)

(73) Assignee: Golden Biotechnology Corporation, Jersey City, NJ (US)

( * ) Notice: Subject to any disclaimer, the term of this patent is extended or adjusted under 35 U.S.C. 154(b) by 196 days.

(21) Appl. No.: 14/086,815

(22) Filed: Nov. 21, 2013

(65) Prior Publication Data
US 2014/0142194 A1 May 22, 2014

Related U.S. Application Data

(60) Provisional application No. 61/729,295, filed on Nov. 21, 2012.

(51) Int. Cl.
*A61K 31/122* (2006.01)
*A61K 36/07* (2006.01)

(52) U.S. Cl.
CPC ............ *A61K 31/122* (2013.01); *A61K 36/07* (2013.01)

(58) Field of Classification Search
CPC .............................. A61K 31/122; A61K 36/07
See application file for complete search history.

(56) References Cited

U.S. PATENT DOCUMENTS 7,342,137 B1 * 3/2008 Liu ....................... A61K 36/07
568/377
2012/0071426 A1 3/2012 Liu et al.

FOREIGN PATENT DOCUMENTS

WO WO2013/148701 A1 10/2013

OTHER PUBLICATIONS

Antonarkis et. al., Trends in Molecular Medicine, 2006, Elsevier Ltd, vol. 12, No. 10, pp. 473-479.*
Sacco et. al., British Journal of Pharmacology, 2003, Nature Publishing Group, vol. 139, pp. 641-651.*
Hudkins et. al., Bioorganic and Medicinal Chemistry Letters, 1998, Pergamon, vol. 8, pp. 1873-1876.*
Singh et. al., Progress in Neurobiology, 2007, Elsevier, vol. 81, pp. 29-44.*
Lindvall et. al., Nature, 2006, Nature Publishing Group, vol. 441, pp. 1094-1096.*
Miklossy et. al., Neurobiology of Aging, 2010, Elsevier, vol. 31, pp. 1503-1515.*
Bonnelli et. al., Expert Opinion in Pharmacotherapeutics, 2007, Informa UK Ltd, vol. 8, No. 2, pp. 141-153.*
Graziano et. al., Current Neurology and Neuroscience Reports, 2009, Current Medicine Group, vol. 9, pp. 423-429.*
Wang et. al., Applied Microbiology and Biotechnology, 2012, Springer-Verlag, vol. 94, pp. 1505-1519.*
Chang, Chi-Huang, et al., "Antrodia cinnamomea Exhibits a Potent Neuroprotective Effect in the PC12 Cell-A[beta]$_{25\text{-}35}$ Model-Pharmacologically through Adenosine Receptors and Mitochondrial Pathway," Planta Medica, vol. 78, No. 17, Oct. 11, 2012, 1813-1823.
Liu, Der-Zen, et al., "Comparative anti-inflammatory characterization of wild fruiting body, liquid-state fermentation, and solid-state culture of Taiwanofungus camphoratus in microglia and the mechanism of its action," J Ethnopharmacol. Aug. 15, 2007;113(1):45-53.
Lee TH., et al., "A new cytotoxic agent from solid-state fermented mycelium of Antrodia camphorata," Planta Med. Oct. 2007;73(13):1412-5.

* cited by examiner

*Primary Examiner* — Sarah Pihonak
(74) *Attorney, Agent, or Firm* — Chang-Hsing Liang

(57) ABSTRACT

The present invention provides methods and compositions for treating neurodegenerative diseases by cyclohexenone compounds.

18 Claims, 2 Drawing Sheets

FIG. 1A-B
A
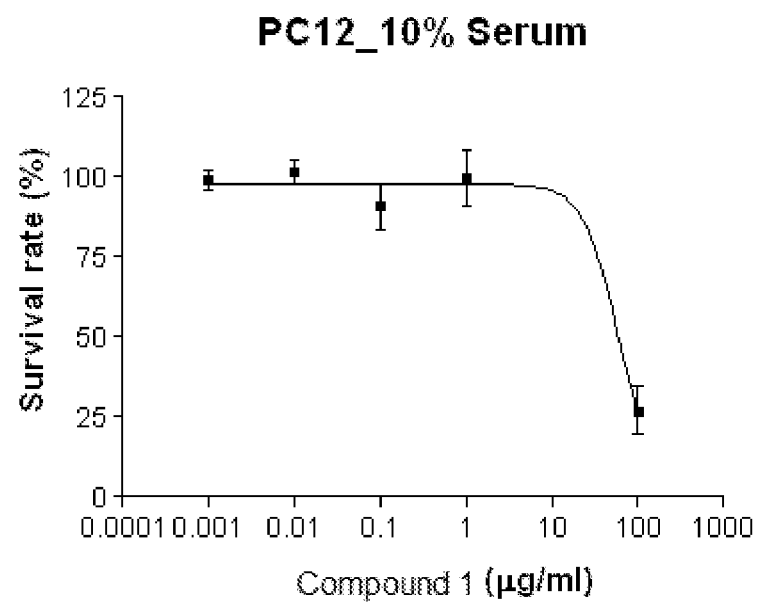
B
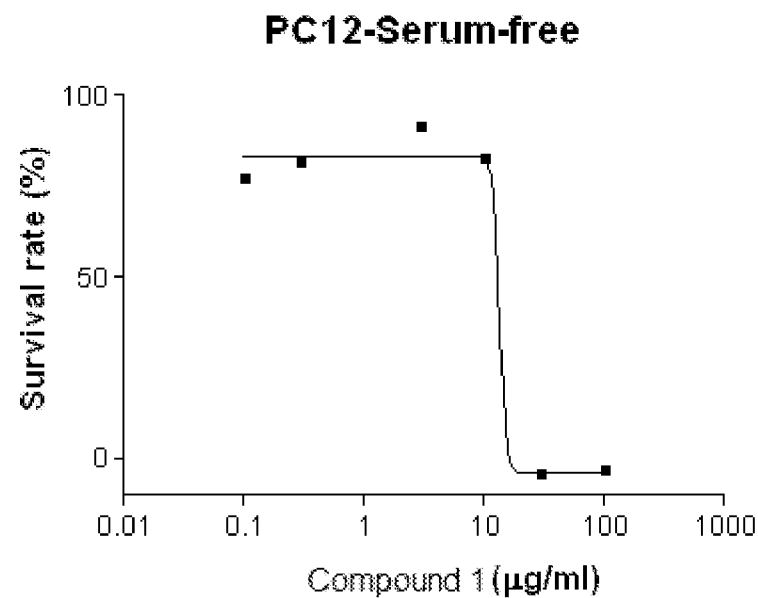

METHODS AND COMPOSITIONS FOR TREATING NEURODEGENERATIVE DISEASES

CROSS REFERENCE

This application claims the benefit of U.S. provisional application Ser. No. 61/729,295, filed Nov. 21, 2012, which is incorporated by reference in its entirety.

BACKGROUND OF THE INVENTION

Neurodegeneration is the umbrella term for the progressive loss of structure or function of neurons, including death of neurons. Many neurodegenerative diseases including Parkinson's disease, Alzheimer's disease, and Huntington's disease occur as a result of neurodegenerative processes. Neurodegeneration can be found in many different levels of neuronal circuitry ranging from molecular to systemic.

Alzheimer's disease (AD) is characterised by loss of neurons and synapses in the cerebral cortex and certain subcortical regions. AD individuals show 70% loss of locus coeruleus cells that provide norepinephrine. Norepinephrine, in addition to its neurotransmitter role, locally diffuses from "varicosities" as an endogenous antiinflammatory agent in the microenvironment around the neurons, glial cells, and blood vessels in the neocortex and hippocampus. It has been shown that norepinephrine stimulates mouse microglia to suppress β-amyloid (Aβ)-induced production of cytokines and their phagocytosis of Aβ. It is estimated that about 18 million people worldwide have AD.

SUMMARY OF THE INVENTION

In one aspect provided herein are methods for treating or reducing the risk of neurodegenerative disease comprising administering to a subject a therapeutically effective amount of a cyclohexenone compound having the structure:

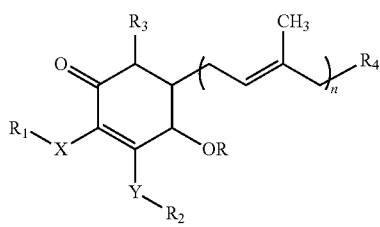

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

In another aspect provided herein are methods for the treatment of a β-Amyloid induced disease in a subject, comprising administering to the subject affected by a disease resulting from hyperglycemia in need a therapeutically effective amount of a cyclohexenone compound having the structure:

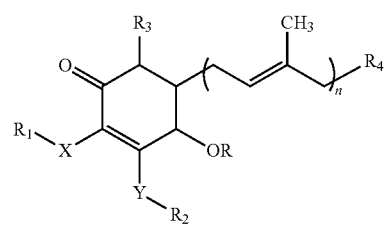

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

In another aspect provided herein are methods for treating Alzheimer's disease in a subject, comprising administering to the subject affected by a disease resulting from hyperglycemia in need a therapeutically effective amount of a cyclohexenone compound having the structure:

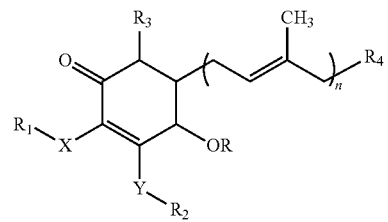

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows viability of PC12 cells treated with exemplary Compound 1. Cells were cultured under 10% serum (A) or serum-free (B) conditions and treated with different concentrations of Compound 1 as indicated for 2 days. Cell viability was detected using Cell Counting Kit-8 (CCK-8). The error bars represented mean±SEM from two independent experiments.

DETAILED DESCRIPTION OF THE INVENTION

Figure 2:
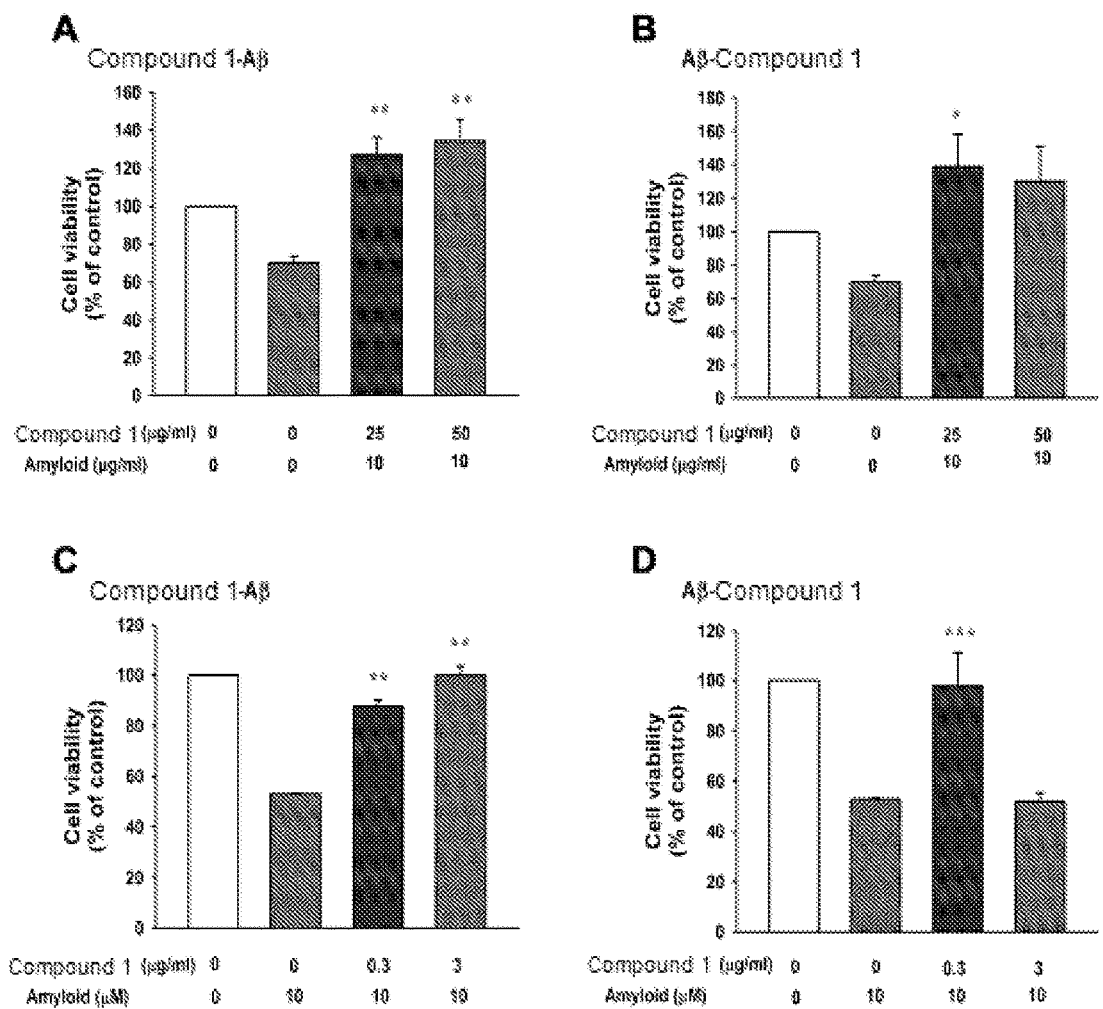
FIG. 2A-D show illustrative effective results of the exemplary cyclohexenone compound such as Compound 1 on cell viability induced by β-amyloid. PC12 cells were cultured under 10% serum (A)(B) or serum-free (C)(D) conditions and pretreated with Compound 1 (A)(C) or β-amyloid (B)(D) as indicated for 24 h. Cell viability was detected using CCK-8. The error bars represented mean±SEM from three independent experiments. * indicated $P<0.05$,  $P<0.01$, and *$P<0.001$ compared with the Aβ-treated control.

The process of neurodegeneration is not well understood so the diseases that stem from it have, as yet, no cures. Several experimental therapeutic agents are in clinical trials. In some embodiments, provided herein are methods for the treatment of neurodegenerative diseases by administering a cyclohexenone compound described herein to a subject (e.g. a human). The cyclohexenone compounds provide therapeutic benefit to a subject being treated for neurodegenerative diseases (see Examples 1-5). The cyclohexenone compounds, in some embodiments, are obtained from extracts of natural products and provide reduced complications and/or side effects. In some embodiments, this invention provides the therapeutic and prophylactic potential of exemplary cyclohexenone compounds (e.g., Compound 1) for treating or reducing the risk of neurodegenerative diseases such as Alzheimer's disease, Parkinson's disease, multiple sclerosis, stroke syndromes, amyotrophic lateral sclerosis, or the like.

The term "neurodegenerative disease (or disorder)" as used herein refers to an abnormality in a mammal in which neuronal integrity is threatened. Neuronal integrity can be threatened when neuronal cells display decreased survival or when the neurons can no longer propagate a signal. Examples of neurodegenerative processes include stroke syndromes, subarachnoid hemorrhage, brain dysfunction post-brain surgery, disorders of the nervous system due to hypoxia, hypoglycemia, brain or spinal damage, intoxication with drugs or gases, administration of chemotherapy, alcohol and the like and examples of neurodegenerative diseases include Alzheimer's disease, amyotrophic lateral sclerosis, Parkinson's disease, myasthenia gravis, HIV-related encephalitis, cervical spondylosis, multiple sclerosis, Down's syndrome, and Huntington's chorea. A key to curing these diseases is control of neuronal death including apoptosis. The cyclohexenone compounds of this invention may be administered systemically to one who is afflicted with neurodegenerative diseases or to patients who are believed to be susceptible to such diseases.

Cellular models composed of primary neuronal cultures or neuron-like cell lines are commonly used to study neuron cell death and to test the neuroprotective properties of specific compounds. Cellular models are easily accessible, permitting dissection and modulation of signaling pathways involved in neuron death. Due to the relative difficulty of studying signaling in neurons, neurotrophin signaling has been primarily studied using the pheochromocytoma PC12 cells as a model system. This cell line has proved useful for studying mechanisms of neuronal survival, differentiation, and cell death. For example, they synthesize, store, and release two common neurotransmitters: dopamine and norepinephrine. PC12 cells release these neurotransmitters in response to potassium ions, acetylcholine, or nicotine, just as a neuron would. Furthermore, PC12 cells exhibit two growth patterns. When they are grown as undifferentiated cells, they divide approximately every 24-48 hours. Second, when PC12 cells are exposed to nerve growth factor (NGF), they exhibit a different growth pattern. Initially, they cease cellular division. Afterwards, they flatten out and develop long projections known as neurites. The neurites often grow to be in close contact with a neighboring cell, resembling a neuronal synapse. If the nerve growth factor is removed, the PC12 cells will eventually return to their roughly spherical shape and resume cell division (Greene et al., (1999) Methodologies for the Culture and Experimental Use of the PC12 Rat Pheochromocytoma Cell Line. In: Culturing Nerve Cells G. Banker, K. Goslin eds., MIT Press, Cambridge, Mass. pp 161-187). NGF withdrawal similarly triggers death of sympathetic neurons both in vivo and in vitro.

To optimize the exemplary Compound 1 concentration for NGF-induced PC12 neural model, titration experiments were performed to determine the $IC_{50}$ values of Compound 1 in PC12. $IC_{50}$ values of the exemplary invention Compound 1 are determined to be 57.98 mg/ml (in 10% serum supplemented media) and 13.39 mg/ml (serum-free media) respectively by cell viability assay (FIG. 1).

To assess the prophylactic potential of the invention cyclohexenone compound (i.e., Compound 1) the NGF-induced PC12 cells were pretreated with different concentrations of Compound 1 (25 and 50 mg/ml in 10% serum-supplemented medium; 0.3 and 3 mg/ml in serum-free medium) and then challenged with 10 μM β-Amyloid (Aβ) before determination of cell viability. The cell viability results indicate that the exemplary Compound 1 exhibits a significant impact in preventing (reducing the risk of) cells from Aβ-induced neuronal damage in either serum or serum-free culture conditions (FIGS. 2A and 2C). The similar experiment was conducted to assess the therapeutic effect of Compound 1. PC12 cells were pretreated with 10 μM Aβ for 24 h in serum and serum-free medium separately first and then challenged with different concentrations of Compound 1 before determination of the cell viability. The results show that the treatment with low-dose Compound 1 dramatically inhibits the damage induced by Aβ and improves the cell viability (FIGS. 2B and 2D).

Clearly, the exemplary cyclohexenone compounds, such as Compound 1, exhibit therapeutic and prophylactic effectiveness in NGF-induced PC12 neural model. Thus, the invention cyclohexenone compounds provided herein such as Compound 1 are useful for preventing or treating neurodegenerative disease such as AD.

In some embodiments, there are provided methods for treating or reducing the risk of neurodegenerative disease comprising administering to a subject a therapeutically effective amount of a cyclohexenone compound having the structure:

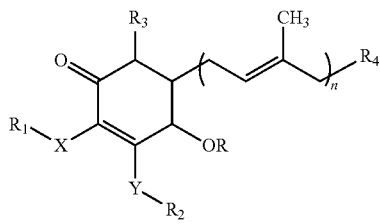

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the methods inhibit β-Amyloid induced neuronal damage in a subject. In some embodiments, the neurodegenerative disease is selected from the group consisting of Alzheimer's disease, Parkinson's disease, multiple sclerosis, stroke syndromes, and amyotrophic lateral sclerosis. In certain embodiments, the neurodegenerative disease is Alzheimer's disease. In some embodiments, the cyclohexenone compound inhibits β-Amyloid induced neuronal damage in a subject. In some embodiments, the subject is human. See Examples 2-5.

In some embodiments, the cyclohexenone compound having the structure

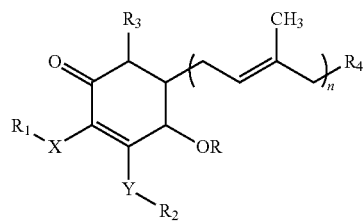

is prepared synthetically or semi-synthetically from any suitable starting material. In other embodiments, the cyclohexenone compound is prepared by fermentation, or the like. For example, Compound 1 (also known as Antroquinonol™ or "Antroq") or Compound 3, in some instances, is prepared from 4-hydroxy-2,3-dimethoxy-6-methylcyclohexa-2,5-dienone. The non-limited exemplary compounds are illustrated below.

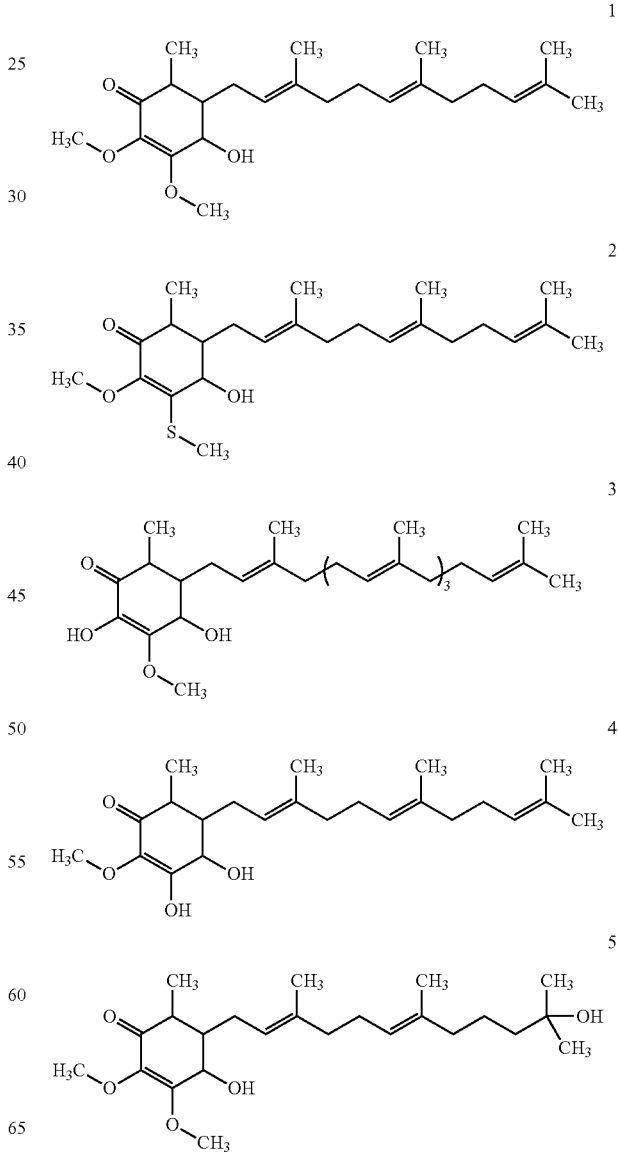

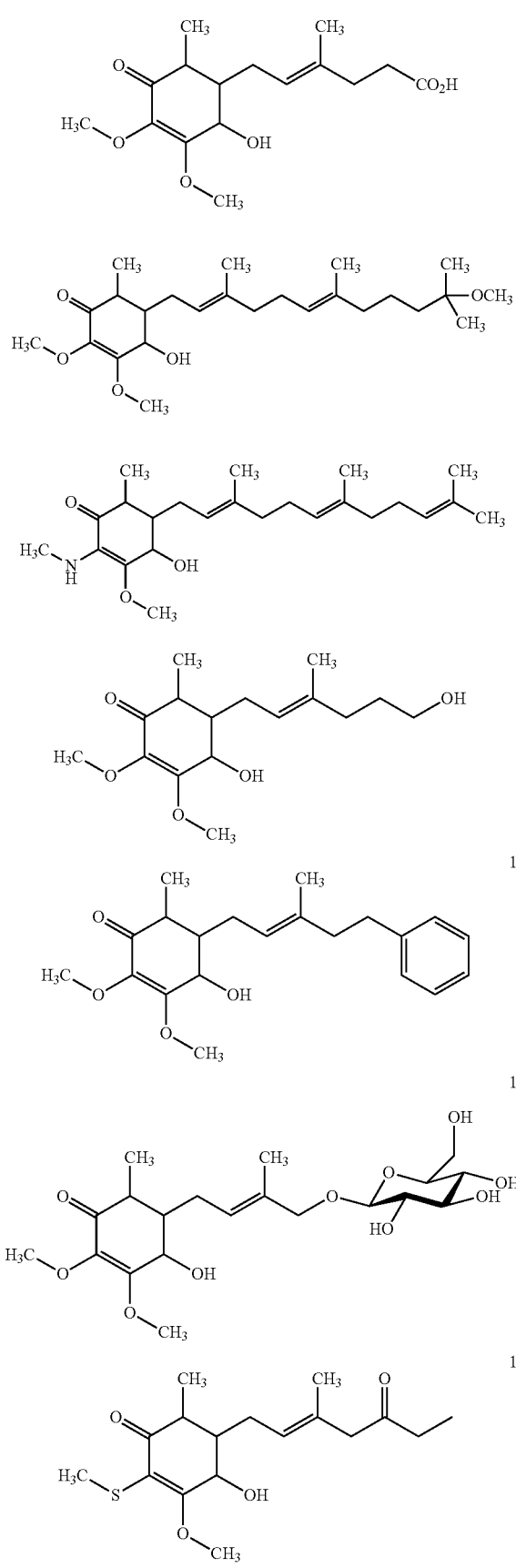
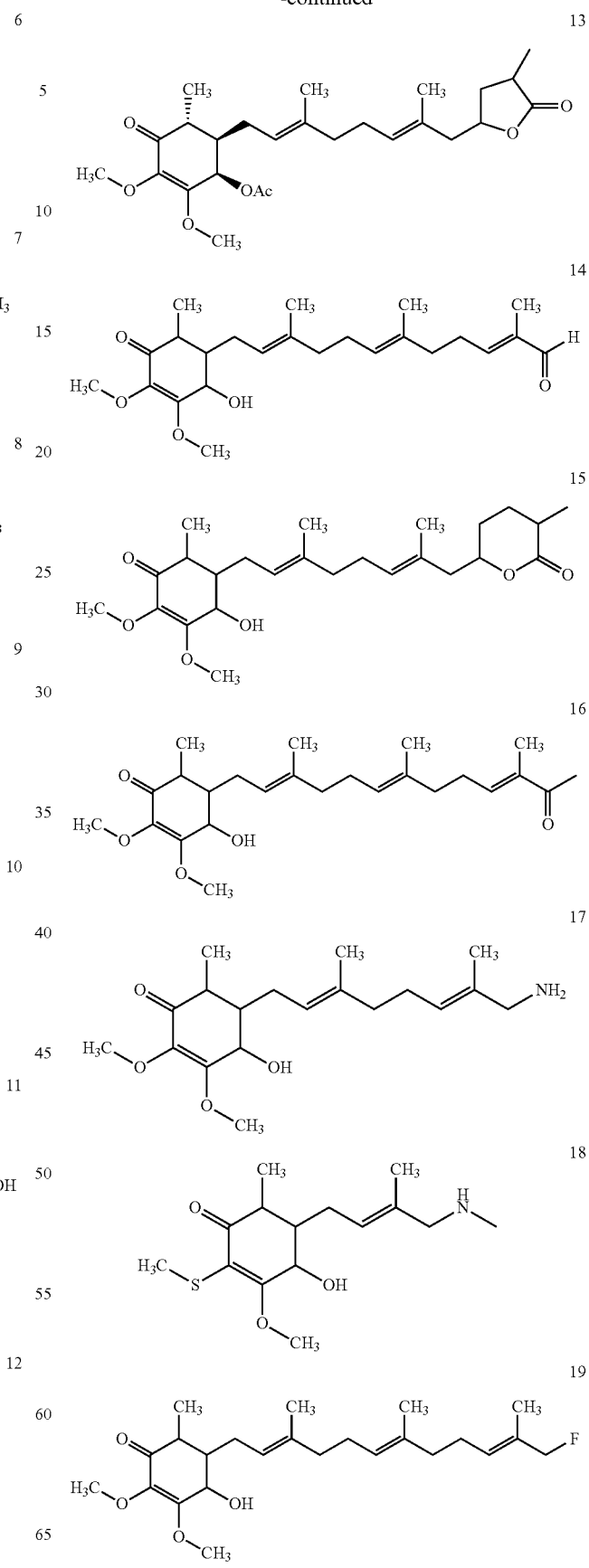

-continued

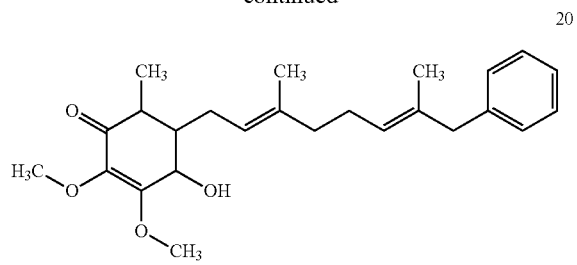

In other embodiments, the cyclohexenone compound having the structure

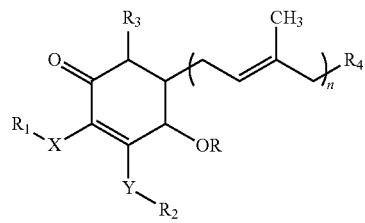

is isolated from the organic solvent extracts of *Antrodia camphorata*. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, and the like), and the like. For example, exemplary Compounds 1-7 are isolated from organic solvent extracts. In certain embodiments, the organic solvent is alcohol. In certain embodiments, the alcohol is ethanol. In some embodiments, the cyclohexenone compound is isolated from the aqueous extracts of *Antrodia camphorata*.

In some embodiments, R is a hydrogen, $C(=O)C_3H_8$, $C(=O)C_2H_5$, or $C(=O)CH_3$. In some embodiments, $R_1$ is a hydrogen or methyl. In certain embodiments, $R_2$ is a hydrogen, methyl, ethyl, propyl, butyl, pentyl or hexyl. In some embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In some embodiments, $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, $C_1$-$C_8$ alkyl, $C_2$-$C_8$alkenyl, $C_2$-$C_8$alkynyl, aryl, and glucosyl, wherein the 5 or 6-membered lactone, $C_1$-$C_8$ alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2CH=C(CH_3)_2$. In certain embodiments, the compound is

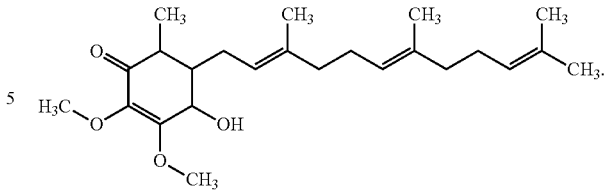

In some embodiments, there are provided methods treating a β-Amyloid induced disease in a subject, comprising administering to the subject affected by a disease resulting from hyperglycemia in need a therapeutically effective amount of a cyclohexenone compound having the structure:

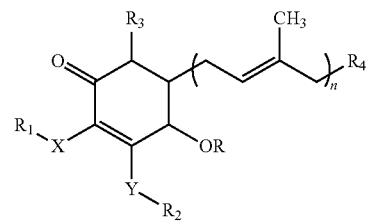

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

In some embodiments, the β-Amyloid induced disease is Alzheimer's disease or Down's syndrome. In certain embodiments, the subject is human.

Certain Pharmaceutical and Medical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched, or straight chain.

The "alkyl" group may have 1 to 12 carbon atoms (whenever it appears herein, a numerical range such as "1 to 12 refers to each integer in the given range; e.g., "1 to 12 carbon atoms" means that the alkyl group may consist of 1 carbon atom, 2 carbon atoms, 3 carbon atoms, etc., up to and including 12 carbon atoms, although the present definition also covers the occurrence of the term "alkyl" where no numerical range is designated). The alkyl group of the compounds described herein may be designated as "$C_1$-$C_8$ alkyl" or similar designations. By way of example only, "$C_1$-$C_8$ alkyl" indicates that there are one, two, three, four, five, six, seven or eight carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a $C_1$-$C_8$ alkyl.

The term "alkylene" refers to a divalent alkyl radical. Any of the above mentioned monovalent alkyl groups may be an alkylene by abstraction of a second hydrogen atom from the alkyl. In one aspect, an alkylene is a $C_1$-$C_{12}$alkylene. In another aspect, an alkylene is a $C_1$-$C_8$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). In one aspect, an arylene is a $C_6$-$C_{10}$ arylene. Exemplary arylenes include, but are not limited to, phenyl-1,2-ene, phenyl-1,3-ene, and phenyl-1,4-ene.

The term "aromatic" refers to a planar ring having a delocalized π-electron system containing 4n+2 π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "halo" or, alternatively, "halogen" or "halide" means fluoro, chloro, bromo or iodo.

The term "lactone" refers to a cyclic ester which can be seen as the condensation product of an alcohol group —OH and a carboxylic acid group —COOH in the same molecule. It is characterized by a closed ring consisting of two or more carbon atoms and a single oxygen atom, with a ketone group =O in one of the carbons adjacent to the other oxygen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein, means a straight, branched chain, or cyclic (in which case, it would also be known as a "cycloalkenyl") hydrocarbon containing from 2-10 carbons and containing at least one carbon-carbon triple bond formed by the removal of four hydrogens. In some embodiments, depending on the structure, an alkynyl group is a monoradical or a diradical (i.e., an alkynylene group). In some embodiments, alkynyl groups are optionally substituted. Illustrative examples of alkynyl include, but are not limited to, ethynyl, propynyl, butynyl, pentynyl, hexynyl, heptynyl, and the like.

The term "alkoxy" as used herein, means an alkyl group, as defined herein, appended to the parent molecular moiety through an oxygen atom. Illustrative examples of alkoxy include, but are not limited to, methoxy, ethoxy, propoxy, 2-propoxy, butoxy, tert-butoxy, pentyloxy, and hexyloxy.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

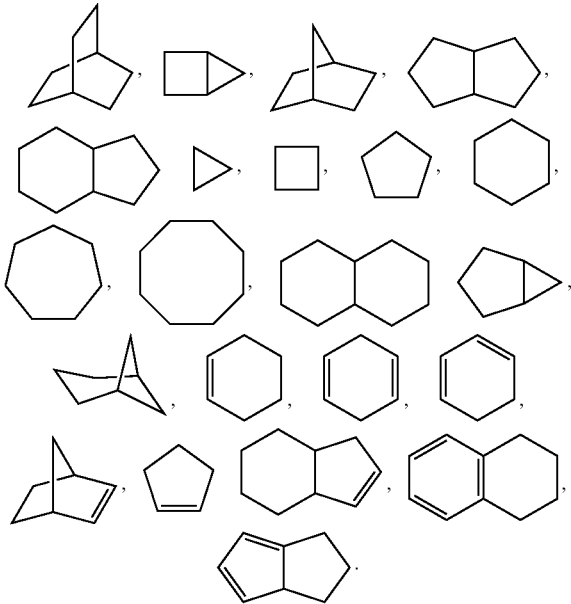

In some embodiments, depending on the structure, a cycloalkyl group is a monoradical or a diradical (e.g., a cycloalkylene group).

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "glucosyl" as used herein, include D- or L-form glucosyl groups, in which the glucosyl group is attached via any hydroxyl group on the glucose ring.

The term "acceptable" with respect to a formulation, composition or ingredient, as used herein, means having no persistent detrimental effect on the general health of the subject being treated.

*Antrodia* is a genus of fungi in the family Meripilaceae. *Antrodia* species have fruiting bodies that typically lie flat or spread out on the growing surface, with the hymenium exposed to the outside; the edges may be turned so as to form narrow brackets. Most species are found in temperate and boreal forests, and cause brown rot.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., a cyclohexenone compound described herein) and a co-agent, are both administered to a patient simultaneously in the form of a single entity or dosage. The term "non-fixed combination" means that the active ingredients, e.g. a compound (i.e., a cyclohexenone compound described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a cyclohexenone compound described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration and Dosage

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, the cyclohexenone compound, or a pharmaceutically acceptable salt, metabolite, solvate or prodrug thereof, is administered parenterally or intravenously. In other embodiments, the cyclohexenone compound, or a pharmaceutically acceptable salt, metabolite, solvate or prodrug thereof, is administered by injection. In some embodiments, the cyclohexenone compound, or a pharmaceutically acceptable salt, metabolite, solvate or prodrug thereof, is administered orally.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the compounds may be given continuously or temporarily suspended for a certain length of time (i.e., a "drug holiday").

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Pharmaceutical Formulation

In some embodiments provide pharmaceutical compositions comprising a therapeutically effective amount of a cyclohexenone compound having the structure:

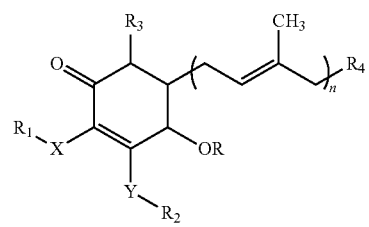

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof; and a pharmaceutically acceptable excipient.

In some embodiments, the cyclohexenone compounds of the pharmaceutical compositions have the structure:

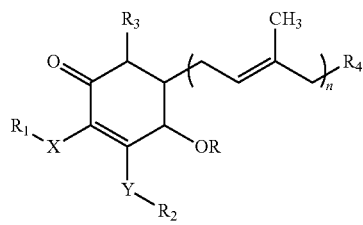

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, R is a hydrogen, $C(=O)C_3H_8$, $C(=O)C_2H_5$, or $C(=O)CH_3$. In some embodiments, each of $R_1$, $R_2$ and $R_3$ independently is a hydrogen, methyl, ethyl, propyl, butyl, pentyl hexyl, heptyl, or octyl. In certain embodiments, $R_1$ is a hydrogen or methyl. In certain embodiments, $R_2$ is a hydrogen, methyl, ethyl, propyl, butyl, pentyl or hexyl. In certain embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In certain embodiments, $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, or glucosyl, wherein the 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, $C_1$-$C_8$ alkyl, 5 or 6-membered lactone, aryl, or glucosyl, wherein the 5 or 6-membered lactone, $C_1$-$C_8$ alkyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

In certain embodiments, the compound is selected from group consisting of

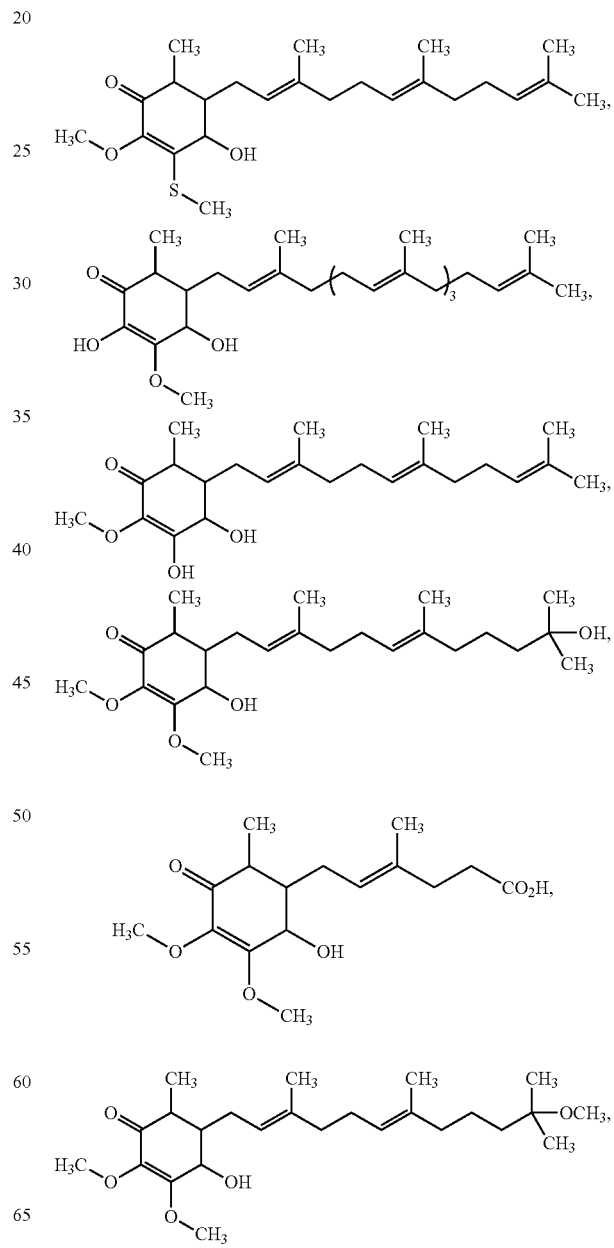

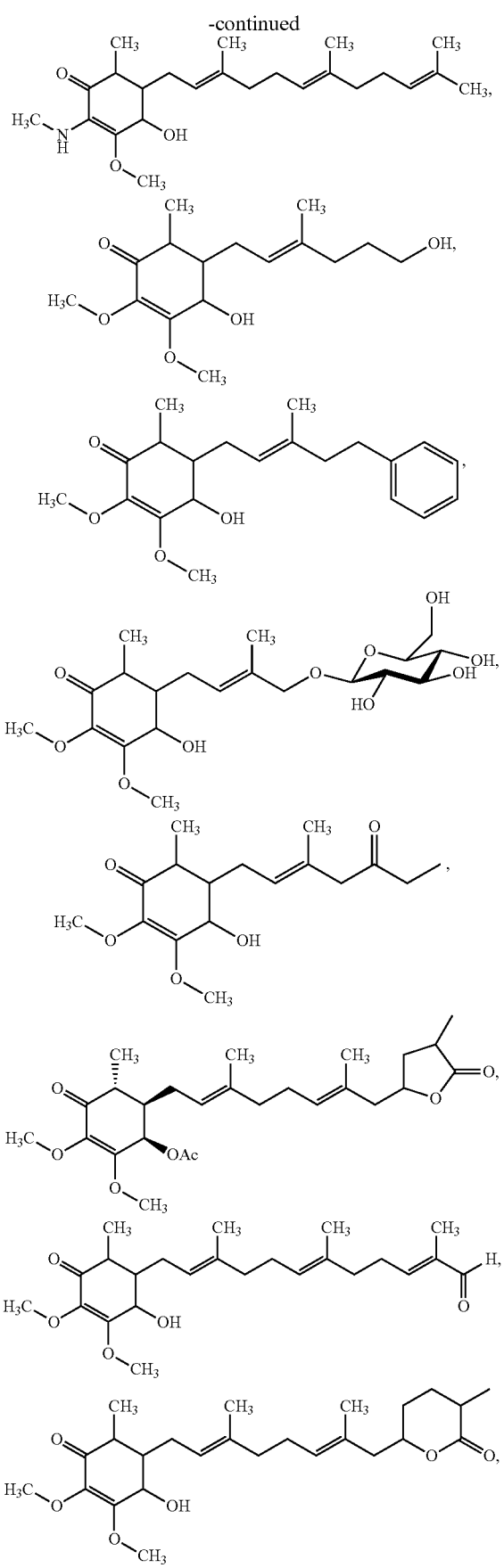
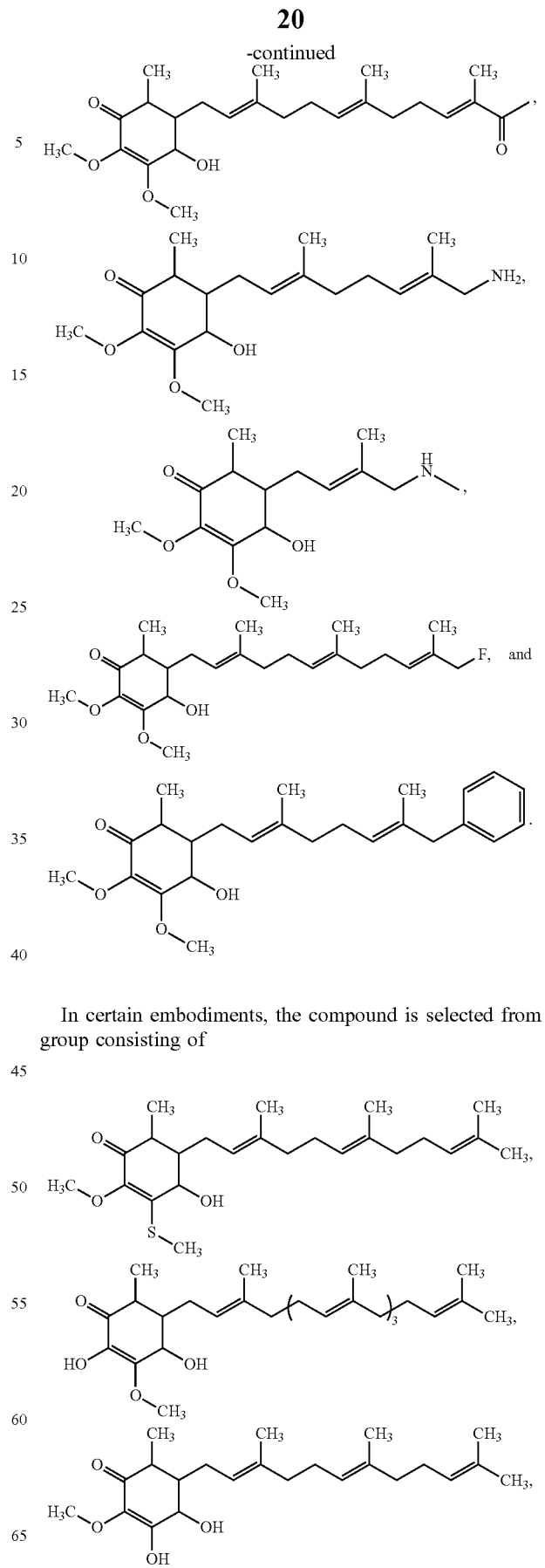
In certain embodiments, the compound is selected from group consisting of

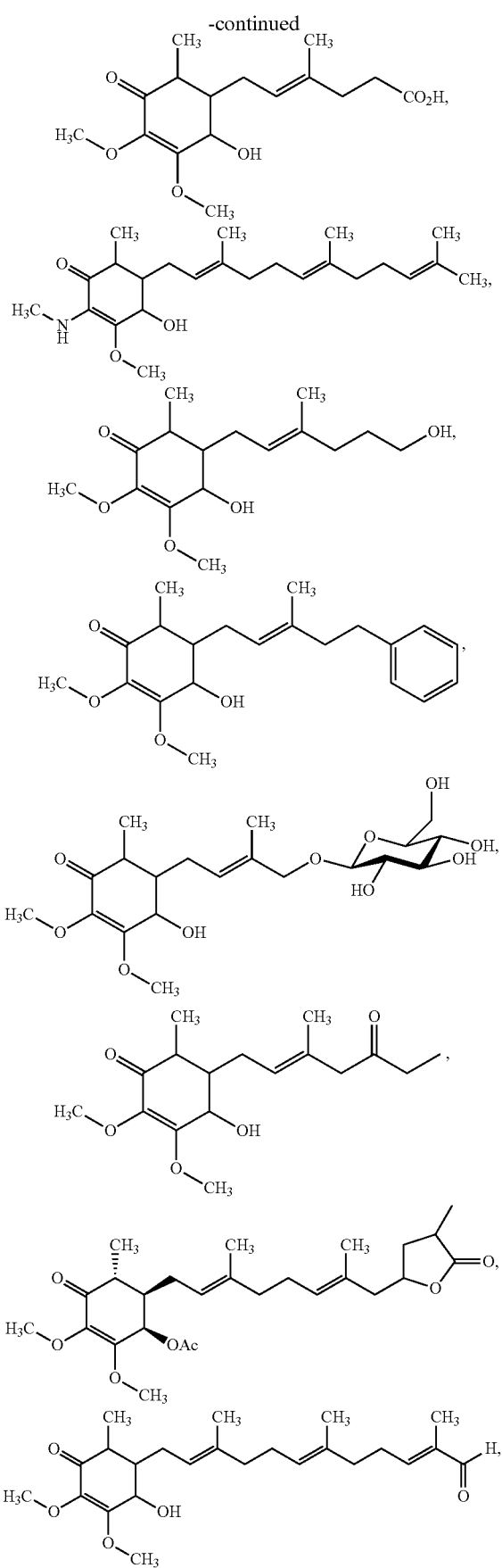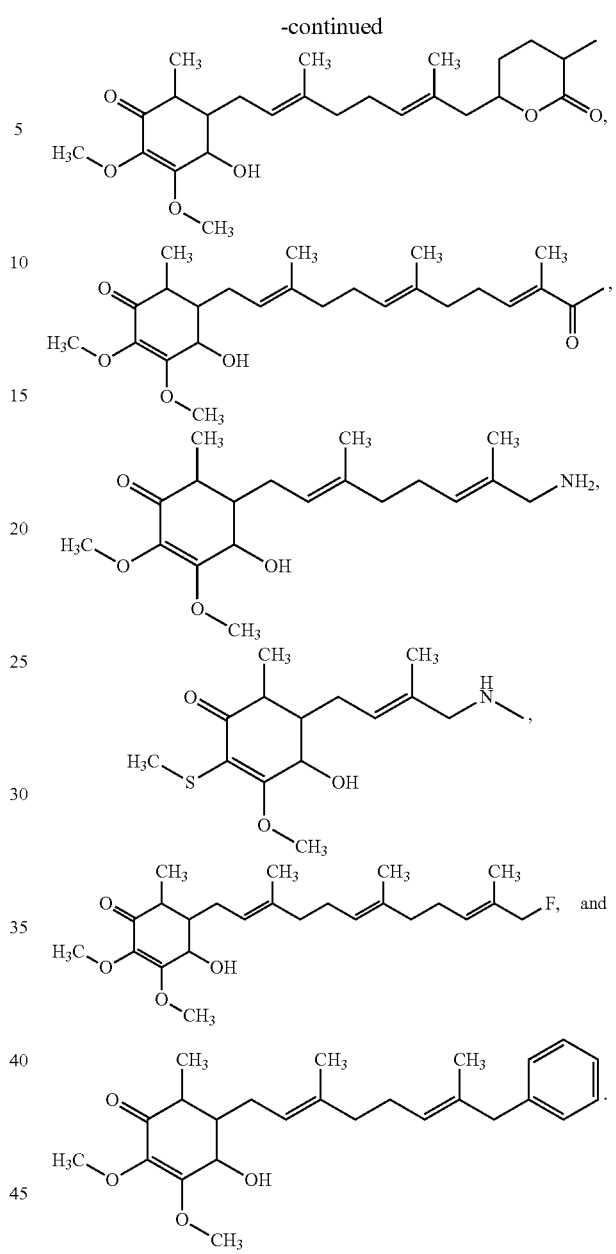

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

Provided herein are pharmaceutical compositions comprising a compound (i.e., a cyclohexenone compound described herein) and a pharmaceutically acceptable diluent(s), excipient(s), or carrier(s). In certain embodiments, the compounds described are administered as pharmaceutical compositions in which a compound (i.e., a cyclohexenone compound described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a cyclohexenone compound described herein).

A pharmaceutical composition, as used herein, refers to a mixture of a compound (i.e., a cyclohexenone compound described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., a cyclohexenone compound described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a cyclohexenone compound described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a cyclohexenone compound described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., a cyclohexenone compound described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a cyclohexenone compound described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., cyclohexenone compounds described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a cyclohexenone compound described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL, 0.6 mL, 1.0 mL or other suitable volume of solution at about a concentration of 0.5 mg to 50 mg of a compound (i.e., a cyclohexenone compound described herein) per 1 mL of solution. Each injector is capable of delivering only one dose of the compound.

In still other embodiments, the compounds (i.e., cyclohexenone compounds described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., cyclohexenone compounds described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., a cyclohexenone compound described herein) is accomplished by means of iontophoretic patches and the like. In certain embodiments, transdermal patches provide controlled delivery of a compound (i.e., a cyclohexenone compound described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., a cyclohexenone compound described herein); (2) a penetration enhancer; and (3) an aqueous adjuvant. In addition, transdermal formulations can include additional components such as, but not limited to, gelling agents, creams and ointment bases, and the like. In some embodiments, the transdermal formulations further include a woven or non-woven backing material to enhance absorption and prevent the removal of the transdermal formulation from the skin. In other embodiments, the transdermal formulations described herein maintain a saturated or supersaturated state to promote diffusion into the skin.

In other embodiments, the compounds (i.e., cyclohexenone compounds described herein) are formulated for administration by inhalation. Various forms suitable for administration by inhalation include, but are not limited to, aerosols, mists or powders. Pharmaceutical compositions of a compound (i.e., a cyclohexenone compound described herein) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatins for use in an inhaler or insufflator are formulated containing a powder mix of the compound and a suitable powder base such as lactose or starch.

Intranasal formulations are known in the art and are described in, for example, U.S. Pat. Nos. 4,476,116, 5,116,817 and 6,391,452, each of which is specifically incorporated herein by reference. Formulations, which include a compound (i.e., a cyclohexenone compound described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds (i.e., cyclohexenone compounds described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., a cyclohexenone compound described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., cyclohexenone compounds described herein) described herein as an active ingredient. The active ingredient is in free-acid or free-base form, or in a pharmaceutically acceptable salt form. In addition, the methods and pharmaceutical compositions described herein include the use crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., cyclohexenone compounds described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., cyclohexenone compounds described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Combination Treatments

In general, the compositions described herein and, in embodiments where combinational therapy is employed, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

Combinations of compounds (i.e., the cyclohexenone compound described herein) with other neurodegenerative disease therapeutic agents are intended to be covered. In some embodiments, examples of neurodegenerative disease such as AD therapeutic agents include, but are not limited to, the following: donepezil (Aricept®), Galantamine (RAZADYNE™, Reminyl®), rivastigmine (Exelon®), tacrine (Cognex®), memantine (Namenda®), and the like.

The combinations of the cyclohexenone compounds and other neurodegenerative disease therapeutic agents described herein encompass additional therapies and treatment regimens with other agents in some embodiments. Such additional therapies and treatment regimens can include another neurodegenerative disease therapy in some embodiments. Alternatively, in other embodiments, additional therapies and treatment regimens include other agents used to treat adjunct conditions associated with the neurodegenerative disease or a side effect from such agent in the combination therapy. In further embodiments, adjuvants or enhancers are administered with a combination therapy described herein.

In some embodiments provide compositions for treating or reducing the risk of neurodegenerative diseases comprising a therapeutically effective amount of a cyclohexenone compound having the structure:

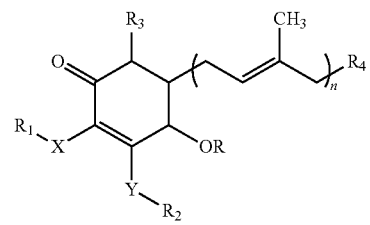

wherein each of X and Y independently is oxygen, NR$_5$ or sulfur;

R is a hydrogen or C(=O)C$_1$-C$_8$alkyl;

each of R$_1$, R$_2$ and R$_3$ independently is a hydrogen, methyl or (CH$_2$)$_m$—CH$_3$;

R$_4$ is NR$_5$R$_6$, OR$_5$, OC(=O)R$_7$, C(=O)OR$_5$, C(=O)R$_5$, C(=O)NR$_5$R$_6$, halogen, 5 or 6-membered lactone, C$_1$-C$_8$alkyl, C$_2$-C$_8$alkenyl, C$_2$-C$_8$alkynyl, aryl, glucosyl, wherein the 5 or 6-membered lactone, C$_1$-C$_8$alkyl, C$_2$-C$_8$alkenyl, C$_2$-C$_8$alkynyl, aryl, and glucosyl are optionally substituted with one or more substituents selected from NR$_5$R$_6$, OR$_5$, OC(=O)R$_7$, C(=O)OR$_5$, C(=O)R$_5$, C(=O)NR$_5$R$_6$, C$_1$-C$_8$ alkyl, C$_2$-C$_8$ alkenyl, C$_2$-C$_8$ alkynyl, C$_3$-C$_8$ cycloalkyl, and C$_1$-C$_8$ haloalkyl;

each of R$_5$ and R$_6$ is independently a hydrogen or C$_1$-C$_8$alkyl;

R$_7$ is a C$_1$-C$_8$alkyl, OR$_5$ or NR$_5$R$_6$;

m=1-12; and n=1-12; or a pharmaceutically acceptable salt, metabolite, solvate or prodrug thereof; and one or more neurodegenerative disease therapeutic agents.

EXAMPLES

Example 1. Preparation of the Exemplary Cyclohexenone Compounds

One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and 0.45 μm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.3% acetic acid (B), with the gradient conditions of 0-10 min in 95%-20% B, 10-20 min in 20%-10% B, 20-35 min in 10%-10% B, 35-40 min in 10%-95% B, at the flow rate of 1 ml/min. The column effluent was monitored with a UV-visible detector.

The fractions collected at 21.2 to 21.4 min were collected and concentrated to yield compound 5, a product of pale yellow liquid. Compound 5 was analyzed to be 4-hydroxy-5-(11-hydroxy-3,7,11-trimethyldodeca-2,6-dienyl)-2,3-dimethoxy-6-methylcyclohex-2-enone with molecular weight of 408 (Molecular formula: $C_{24}H_{40}O_5$). $^1$H-NMR (CDCl$_3$) δ (ppm)=1.21, 1.36, 1.67, 1.71, 1.75, 1.94, 2.03, 2.07, 2.22, 2.25, 3.68, 4.05, 5.71 and 5.56. $^{13}$C-NMR (CDCl$_3$) δ(ppm): 12.31, 16.1, 16.12, 17.67, 25.67, 26.44, 26.74, 27.00, 30.10, 40.27, 43.34, 59.22, 60.59, 71.8, 120.97, 123.84, 124.30, 131.32, 134.61, 135.92, 138.05, 160.45, and 197.11.

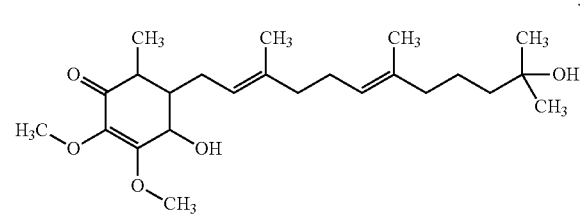

Compound 5: 4-hydroxy-5-(11-hydroxy-3,7,11-trimethyldodeca-2,6-dienyl)-2,3-dimethoxy-6-methylcyclohex-2-enone The fractions collected at 23.7 to 24.0 min were collected and concentrated to yield compound 7, a product of pale yellow liquid. Compound 7 was analyzed to be 4-hydroxy-2,3-dimethoxy-5-(11-methoxy-3,7,11-trimethyldodeca-2,6-dienyl)-6-methylcyclohex-2-enone with molecular weight of 422 ($C_{25}H_{42}O_5$). $^1$H-NMR (CDCl$_3$) δ (ppm)=1.21, 1.36, 1.71, 1.75, 1.94, 2.03, 2.07, 2.22, 2.25, 3.24, 3.68, 4.05, 5.12, 5.50, and 5.61. $^{13}$C-NMR (CDCl$_3$) δ(ppm): 12.31, 16.1, 16.12, 17.67, 24.44, 26.74, 27.00, 37.81, 39.81, 40.27, 43.34, 49.00, 59.22, 60.59, 120.97, 123.84, 124.30, 135.92, 138.05, 160.45 and 197.12.

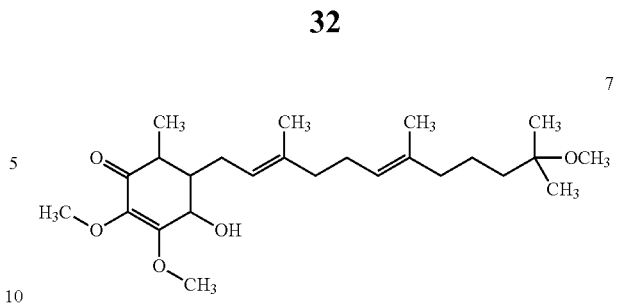

Compound 7: 4-hydroxy-2,3-dimethoxy-5-(11-methoxy-3,7,11-trimethyldodeca-2,6-dienyl)-6-methylcyclohex-2-enone The fractions collected at 25 to 30 min were collected and concentrated to yield 4-hydroxy-2,3-dimethoxy-6-methyl-5-(3,7,11-trimethyldodeca-2,6,10-trienyl)cyclohex-2-enone (compound 1), a product of pale yellow brown liquid. The analysis of compound 1 showed the molecular formula of $C_{24}H_{38}O_4$, molecular weight of 390 with melting point of 48 to 52° C. NMR spectra showed that $^1$H-NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (ppm)=12.31, 16.1, 16.12, 17.67, 25.67, 26.44, 26.74, 27.00, 39.71, 39.81, 40.27, 43.34, 59.22, 60.59, 120.97, 123.84, 124.30, 131.32, 135.35, 135.92, 138.05, 160.45, and 197.12.

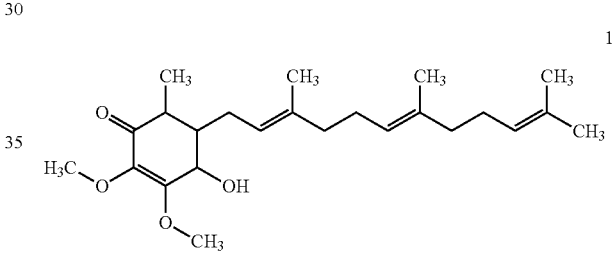

Compound 1: 4-hydroxy-2,3-dimethoxy-6-methyl-5-(3,7,11-trimethyldodeca-2,6,10-trienyl)cyclohex-2-enone Compound 6, a metabolite of compound 1, was obtained from urine samples of rats fed with Compound 1 in the animal study. Compound 6 was determined to be 4-hydroxy-2,3-dimethoxy-6-methyl-5-(3-methyl-2-hexenoic acid)cyclohex-2-enone with molecular weight of 312 ($C_{16}H_{24}O_6$). Compound 4 which was determined as 3,4-dihydroxy-2-methoxy-6-methyl-5-(3,7,11-trimethyldodeca-2,6,10-trienyl)cyclohex-2-enone (molecular weight of 376, $C_{23}H_{36}O_4$), was obtained when compound 1 was under the condition of above 40° C. for 6 hours.

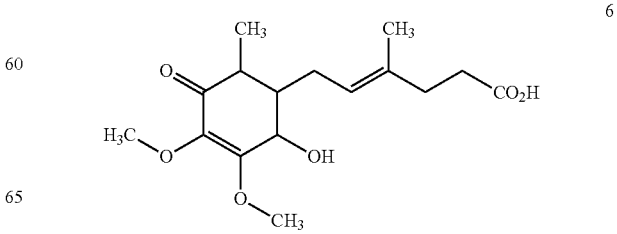

33

-continued

4

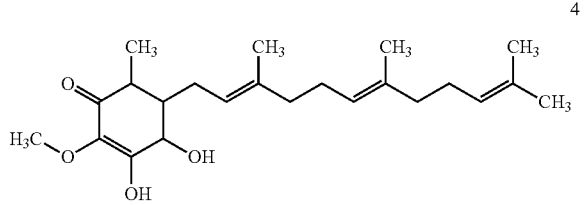

Alternatively, the exemplary compounds may be prepared from 4-hydroxy-2,3-dimethoxy-6-methylcyclohexa-2,5-dienone, or the like. Similarly, other cyclohexenone compounds having the structure

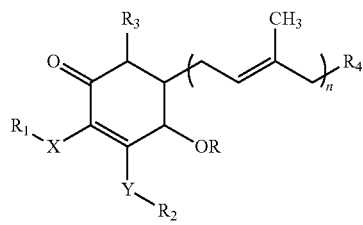

are isolated from *Antrodia camphorata* or prepared synthetically or semi-synthetically from the suitable starting materials. An ordinary skilled in the art would readily utilize appropriate conditions for such synthesis.

Example 2. Preparation and Maintenance of PC12 Cultures

PC12 is a cell line derived from a pheochromocytoma of the rat adrenal medulla. PC12 cells stop dividing and terminally differentiate when treated with nerve growth factor. This makes PC12 cells, and the like, useful as a model system for neuronal differentiation.

Rat pheochromocytoma PC12 cells, purchased from Bioresource Collection and Research Center (BCRC), were cultured in RPMI1640 medium (Gibco, MD) containing 10% fetal calf serum, 5% horse donor serum, 100 µg/ml streptomycin, 100 units/ml penicillin, 2 mM L-glutamine, and maintained in humidified incubator at 37° C. with 5% $CO_2$. Cells were transferred twice a week. Experiments were carried out in 96-well plates coated with poly-$_D$-lysine (1 mg/mL) to assist cell adhesion. PC12 cells were grown on medium with mouse submaxillary-gland nerve growth factor (NGF 2.5S, 100 ng/ml; Invitrogen, Carlsbad, Calif.) for 48 h to induce differentiation into neuron-like cells before all experiments conducted in this study.

Example 3. Experimental Treatments of Compound 1 and β-Amyloid on PC12 Cultures

To optimize the exemplary Compound 1 concentration for NGF-induced PC12 neural model, titration experiments were performed to determine the $IC_{50}$ values of Compound 1 in PC12. PC12 Cells ($1\times10^4$ cells) were incubated with various concentrations of Compound 1 (0.001, 0.01, 0.1, 1, 10, 100 µg/ml in a 10% serum-supplemented medium; 0.3, 1, 3, 10, 30, 100 µg/ml in serum-free medium) for 48 h.

β-Amyloid$_{1-40}$ (Aβ) (Invitrogen, Carlsbad, Calif.) was dissolved in 0.1% (v/v) trifluoroacetic acid (TFA) in water at 10 mg/ml and stored at −20° C. as a stock solution. Aβ was diluted to 0.5 mg/ml with phosphate-buffered saline solution

34

(PBS, without Ca2+) and aggregate at 25° C. for 48 h before use. To investigate the therapeutic effect of exemplary Compound 1 on Alzheimer disease (AD) cell model in vitro, cultures were pretreated with Aβ for 24 h and then exposed to freshly prepared Compound 1 for 24 h before cell viability measurements. In contrast, to investigate the prophylactic effect of Compound 1 on AD cell model, cultures were pretreated with Compound 1 for 24 h and then exposure to aggregated Aβ for 24 h before cell viability measurements.

Example 4: CCK-8 Cell Viability Assay

Cell Counting Kit-8 (CCK-8) allows sensitive colorimetric assays for the determination of cell viability in cell proliferation and cytotoxicity assays. The detection sensitivity of CCK-8 is higher than the other tetrazolium salts such as MTT, XTT, MTS or WST-1.

The viability of cells was measured using the Cell Counting Kit-8 (CCK-8, Enzo, Life Sciences). A highly water-soluble tetrazolium salt, WST-8, is reduced by dehydrogenases in cells to give a yellow-colored product (formazan), which is soluble in the culture medium. The amount of the fomazan dye generated by the activity of dehydrogenases in cells is directly proportional to the number of living cells. After treatments, the CCK-8 solution was added to each well of plates and incubates the plate for 4 h in the incubator. The concentration of the formazan product was determined spectrophotometrically at an absorbance wavelength 450 nm and cell viability was expressed as a percentage of the corresponding control.

$IC_{50}$ values of the exemplary invention Compound 1 are determined to be 57.98 µg/ml (in 10% serum supplemented media) and 13.39 mg/ml (serum-free media) respectively by cell viability assay (FIG. 1). To assess the prophylactic potential of the invention cyclohexenone compound (i.e., Compound 1) the NGF-induced PC12 cells were pretreated with different concentrations of Compound 1 (25 and 50 mg/ml in 10% serum-supplemented medium; 0.3 and 3 µg/ml in serum-free medium) for 24 h. After washing, the cells were then challenged with 10 µM β-Amyloid (Aβ) for another 24 h before determination of cell viability. The cell viability results indicate that the exemplary Compound 1 exhibits a significant impact in preventing (reducing the risk of) cells from Aβ-induced neuronal damage in either serum or serum-free culture conditions (FIGS. 2A and 2C). The similar experiment was conducted to assess the therapeutic effect of Compound 1. PC12 cells were pretreated with 10 µM Aβ for 24 h in serum and serum-free medium separately first. After washing, PC 12 cells were then challenged with different concentrations of Compound 1 as indicated for another 24 h before determination of the cell viability. The results showed that the treatment with low-dose Compound 1 dramatically inhibited the damage induced by Aβ and improved the cell viability (FIGS. 2B and 2D).

Example 5: Animal Study of Parkinson's Disease with Compound 1

Thirty adult Wistar rats are randomly divided into five groups namely control, 6-OHDA model, and Compound 1 (25, 50, and 100 mg/kg body weight suspended in one ml of 0.1% carboxymethyl cellulose). The treatment is started three days before surgery and continued for next 14 days. The surgery is done on third day in all groups for administration of 6-OHDA into the right striatum and right substantia nigra, whereas control group injects with 6-OHDA vehicle. Various behavior and biochemical tests (Apomorphine-induced rotational behavior, Stepping test, Initiation time, Postural balance test, and Disengage time) are used to evaluate the neuroprotective effect of Compound 1. One-way analysis of variance (ANOVA) followed by Dunnett's test is used to compare inter-group differences. P<0.05 is considered as statistically significant.

Animals:

Thirty male adult Wistar rats, weighing 200 to 250 g, are maintained under 12: 12-h light: dark cycle with food and water provided ad libitum.

Experimental Design:

The animals are randomly allocated to five groups as Vehicle, 6-OHDA, Compound 1 (25, 50, and 100 mg/kg body weight) of six rats each. Vehicle and 6-OHDA groups are received 1 ml of 0.1% carboxymethyl cellulose (CMC) solution in water while Compound 1 groups are treated with the selected doses, suspended in 1 ml of 0.1% CMC in water. All treatments are given orally; daily in morning at 10 am, for 17 days (includes three days pre-treatment before surgery). On the third day, brain surgery is performed, after 60 minutes of each treatment, in all groups for 6-OHDA administration except vehicle-treated group where vehicle is administered.

Operative Procedure:

Unilateral striatal lesion is produced by stereotaxic injection of 7 mg 6-OHDA into the right striatum and 7 mg 6-OHDA into the right substantia nigra according to the atlas of known procedure.

Briefly, the animal is anesthetized with pentobarbital anesthesia (Sigma, 45 mg/kg, i.p.) and placed in stereotaxis instruments. The solution is prepared in a 0.2 mg/ml ascorbate saline and injected into right striatum with a Hamilton syringe at a rate of 1 µl/min. The stereotaxic co-ordinates are 1 mm anterior to bregma, 2 mm lateral from midline, and 4.5 mm below the dura for striatum and 5.8 mm posterior to bregma, 1.6 mm lateral from midline, and 8 mm below the dura for SN part of brain with the incisor bar located 3.3 mm below the interaural line on the non-dominant side.

Quantitation of Rotational Behavior:

On 14th day, after right striatum stereotaxic injection of 6-OHDA, animals are subjected to rotational behavior testing. Rats are injected with apomorphine hydrochloride subcutaneously (Sigma, 0.05 mg/kg) and after 15 minutes from injection, contralateral turns are recorded for a 30-minute period. In order to exclude the influence of apomorphine, rotational test is performed at last of the all other behavior test.

Stepping Test:

This test is used for measurement of akinesia. The rat is held with one hand by the experimenter fixing the hind limbs (slightly raising the torso) and with the other hand fixing the forelimb that is not to be monitored. In this way, the other forepaw has to bear the weight. When the rats are moved with a speed of 90 cm per 5 s in forward and backward along the table, the free forelimb has to step with the movement of the experimenter to keep balance. The steps taken to keep balance are recorded as the adjusting steps. This is done for both the contralateral and ipsilateral forepaw and finally counted together. The numbers of adjusting steps for both directions are counted.

Initiation Time:

The rats are pre-trained for two days to turn up a wooden ramp (1.1 m) into their home cage. During the test, the rat is held as per the stepping test. Time is measured until the rat initiated movement with the forelimb is not fixed by the experimenter. This duration is defined as the initiation time and 180 s is used as the break-off point. The test is performed once a day for each forelimb on three consecutive days and the mean of the three test sessions is calculated.

Postural Test:

The rat is held as described for the stepping test and then in a fast movement tilted toward the side of the paw touching the table, which causes a loss of balance. The animal tries to regain balance with an adjusting step that is recorded by a scoring system ranging from 0 to 3: (0) no detectable muscle reaction, the rat falls onto the side; (1) clear forelimb reaction, but the rat cannot move limb under the body toward the center of gravity and thus still falls onto the side; (2) incomplete recovery of balance, i.e., the rat moves its limb under the body but not yet fully into the center of gravity, and thus the forelimb is not aligned vertically to the body; further, the forepaw might not be placed in a plain position on the table and digits might be crossed over each other; (3) complete recovery of balance. The test is repeated six times a day on both sides giving a maximum daily score of 18. Final results are expressed as average of the three-test day's score. Six animals repeat three times every day for three days, then mean calculates from 54 values for six rats in each group.

Disengage Time:

A blunt wooden probe touches the perioral region beneath the vibrissae of the rat repeatedly at 1 s intervals when the rat is engaged in eating a piece of milk chocolate. The latency of the orienting response, i.e., turning of the head toward the stimulus, is recorded; an immediate response is scored as 1 s. Stimulation is discontinued if the animal does not respond within a period of 180 s. The test is performed once a day on each side over two days and the mean of the two subtests is calculated.

All these tests (Rotational test, Stepping test, Initiation time, Postural test, Disengage time) are performed by a blind investigator, not aware of the treatment given to the animals.

Measurement of Dopamine and its Metabolites:

Animals are euthanized day after rotational test to exclude the effect of apomorphine. The striatal samples are separated and weighed immediately after dissection and stored at −70° C. until assay. The striatal samples are sonicated in ice cold 0.2M perchloric acid containing 0.05% ethylenediaminetetraacetic acid (EDTA). The homogenates are immediately centrifuged at 10,000 rpm at 4° C. for 10 minutes. The supernatants are filtered using 0.45-µm pore filters and are used for determination of dopamine (DA) and its metabolites 3,4-dihydroxyphenylacetic acid (DOPAC) and homovanillic acid (HVA) using high-performance liquid chromatography with electrochemical detector. The exemplary mobile phase consists of a mixture of 0.1M citric acid monohydrate, 0.1M sodium acetate, 7% methanol, 100 mM EDTA, and 0.01% sodium octane sulfonic acid. The flow rate of mobile phase is maintained at 1 ml/min and the injection volume is 20 ml.

Statistical Analysis:

Data are expressed as mean±standard error of the mean (SEM). Multiple group comparisons are performed using one-way analysis of variance (ANOVA) follows by Dunnett's test. P<0.05 is considered statistically significant.

Example 6: Randomized, Controlled Study Evaluating Compound 1 in Subjects with Mild to Moderate Alzheimer's Disease Sixty patients with mild to moderate Alzheimer's disease will participate in this study. Half of the study subjects will take Compound 1 orally, while the other half will take a placebo.

Study Design: Allocation: Randomized
Endpoint Classification: Safety/Efficacy Study
Intervention Model: Crossover Assignment
Masking: Double Blind (Subject, Caregiver, Investigator)
Primary Purpose Treatment Primary Outcome Measures:

Alzheimer's Disease Assessment Scale-Cognitive Subscale 75 (ADAS-Cog 75) at Week 6 [Time Frame: Week 6]

12-item scale to assess severity of cognitive impairment in AD. Items include word recall, naming objects and fingers, following commands, constructional praxis, ideational praxis, orientation, word recognition, spoken language ability, comprehension of spoken language, word finding difficulty in spontaneous speech, remembering test instructions, and concentration/distractibility. Total score range from 0-75 with 75 indicating worse cognition.

Secondary Outcome Measures:

Alzheimer's Disease Assessment Scale-Cognitive Subscale 75 (ADAS-Cog 75) at Week 3 [Time Frame: Week 3]

11-item scale designed to assess the severity of cognitive impairments in AD subjects. Items include word recall, naming objects and fingers, following commands, constructional praxis, ideational praxis, orientation, word recognition, spoken language ability, comprehension of spoken language, word finding difficulty in spontaneous speech, and remembering test instructions. Total score range from 0-70 with 70 indicating worse cognition.

Alzheimer's Disease Assessment Scale-Cognitive Subscale 70 (ADAS-Cog 70) at Week 6 [Time Frame: Week 6]

11-item scale designed to assess the severity of cognitive impairments in AD subjects. Items include word recall, naming objects and fingers, following commands, constructional praxis, ideational praxis, orientation, word recognition, spoken language ability, comprehension of spoken language, word finding difficulty in spontaneous speech, and remembering test instructions. Total score range from 0-70 with 70 indicating worse cognition.

Alzheimer's Disease Assessment Scale-Cognitive Subscale 70 (ADAS-Cog 70) at Week 6 [Time Frame: Week 6]

11-item scale designed to assess the severity of cognitive impairments in AD subjects. Items include word recall, naming objects and fingers, following commands, constructional praxis, ideational praxis, orientation, word recognition, spoken language ability, comprehension of spoken language, word finding difficulty in spontaneous speech, and remembering test instructions. Total score range from 0-70 with 70 indicating worse cognition.

Mean Clinical Global Impression—Improvement (CGI-I) Score at Week 6 [Time Frame: Week 6]

CGI-I: 7-point clinician rated scale ranging from 1 (very much improved) to 7 (very much worse) Improvement is defined as a score of 1 (very much improved), 2 (much improved), or 3 (minimally improved) on the scale. Higher score=more affected.

Neuropsychiatric Inventory (NPI) Total Score at Week 3 [Time Frame: Week 3]

Caregiver interview-based rating scale assessing 12 behavioral disturbances occurring in dementia: delusions, hallucinations, agitation/aggression, depression/dysphoria, anxiety, elation/euphoria, apathy/indifference, disinhibition, irritability/lability, aberrant motor behavior, appetite/eating, and sleep. Each symptom score derived by frequency of symptoms*severity of symptoms (range 0-12). Total score=sum of symptom scores; range: 0-144 with higher score indicating greater behavioral disturbances.

Neuropsychiatric Inventory (NPI) Total Score at Week 6 [Time Frame: Week 6]

Caregiver interview-based rating scale assessing 12 behavioral disturbances occurring in dementia: delusions, hallucinations, agitation/aggression, depression/dysphoria, anxiety, elation/euphoria, apathy/indifference, disinhibition, irritability/lability, aberrant motor behavior, appetite/eating, and sleep. Each symptom score derived by frequency of symptoms*severity of symptoms (range 0-12). Total score=sum of symptom scores; range: 0-144 with higher score indicating greater behavioral disturbances.

Computerized Test Battery for Cognition (CogState) Tasks: Detection at Week 3 [Time Frame: Week 3]

Assessment of the cognitive domain psychomotor function through yes or no responses within 5 minutes to 30 trials; score range: 0 to 3.69. Performance variable: speed of performance; average of the log 10 t transformed reaction time for correct responses. Reaction times longer than 5 seconds (log 10 [5000]) were excluded as reflecting responses that were abnormally slow.

Computerized Test Battery for Cognition (CogState) Tasks: Detection at Week 6 [Time Frame: Week 6]

Assessment of the cognitive domain psychomotor function through yes or no responses within 5 minutes to 30 trials; score range: 0 to 3.69. Performance variable: speed of performance; average of the log 10 t transformed reaction time for correct responses. Reaction times longer than 5 seconds (log 10 [5000]) were excluded as reflecting responses that were abnormally slow.

In the case wherein the patient's status does improve, upon the doctor's discretion the administration of the compounds may be given continuously or temporarily suspended for a certain length of time by the following design.

| Arms | Assigned Interventions |
|---|---|
| Experimental: Compound 1 | Drug: Compound 1 200 mg once daily for 1 week followed by 100 mg twice daily for 1 week followed by 50 mg twice daily for 4 weeks |
| Placebo Comparator: Placebo | Drug: Placebo Placebo once daily for 1 week followed by placebo twice daily for 5 weeks. |

Eligibility
  Ages Eligible for Study: 55 Years to 85 Years
  Genders Eligible for Study: Both
Criteria
  Inclusion Criteria: Males or females, age 55-85
  Diagnosis of probable Alzheimer's disease, consistent with criteria from both: 1) National Institute of Neurological and Communicable Disease and Stroke and Alzheimer's Disease and Related Disorders Association (NINCDS-ADRDA) and 2) Diagnostic and Statistical Manual of Mental Disorders (DSM IV).
  Mini-mental status exam score of 14-26 inclusive
  Rosen-Modified Hachinski Ischemia Score of < or =4
  Exclusion Criteria:
  Diagnosis or history of other dementia or neurodegenerative disorders
  Diagnosis or history of clinically significant cerebrovascular or cardiovascular disease
  Subjects with pulmonary disease or evidence of clinically significant pulmonary symptoms Example 7: Oral Formulation To prepare a pharmaceutical composition for oral delivery, 100 mg of an exemplary Compound 1 was mixed with 100 mg of corn oil. The mixture was incorporated into an oral dosage unit in a capsule, which is suitable for oral administration.

In some instances, 100 mg of a compound described herein is mixed with 750 mg of starch. The mixture is incorporated into an oral dosage unit for, such as a hard gelatin capsule, which is suitable for oral administration.

Example 8: Sublingual (Hard Lozenge) Formulation

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 9: Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for alleviating, abating or ameliorating at least one symptom of, or reducing the risk of neurodegenerative disease caused by neuronal damage comprising administering to a subject a therapeutically effective amount of a composition consisting of a cyclohexenone compound and one or more physiologically acceptable carriers, and/or excipients, wherein the cyclohexenone compound is of the following structure:

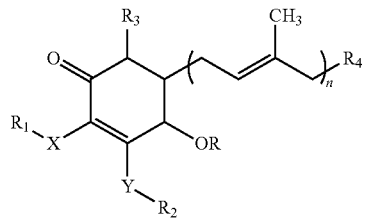

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is 5 or 6-membered lactone, $C_1$-$C_8$alkyl, $C_2$-$C_8$alkenyl, $C_2$-$C_8$alkynyl, aryl, optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
m=1-12; and
n=1-12; or a pharmaceutically acceptable salt, or solvate thereof, wherein said compound inhibits neuronal damage.

2. The method according to claim 1, wherein said method inhibits β-Amyloid induced neuronal damage in a subject.

3. The method of claim 1, wherein said neurodegenerative disease is selected from the group consisting of Alzheimer's disease, Parkinson's disease, multiple sclerosis, stroke syndromes, and amyotrophic lateral sclerosis.

4. The method of claim 3, wherein said neurodegenerative disease is Alzheimer's disease.

5. The method according to claim 1, wherein said cyclohexenone compound inhibits β-Amyloid induced neuronal damage in a subject.

6. A method for alleviating, abating or ameliorating at least one symptom of a β-Amyloid induced disease in a subject, comprising administering to the subject in need a therapeutically effective amount of a composition consisting of a cyclohexenone compound and one or more physiologically acceptable carriers, and/or excipients, wherein the cyclohexenone compound is of the following structure:

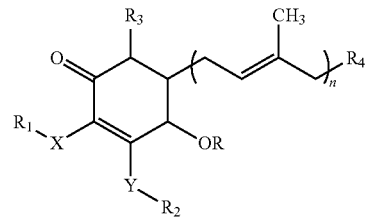

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is 5 or 6-membered lactone, $C_1$-$C_8$alkyl, $C_2$-$C_8$alkenyl, $C_2$-$C_8$alkynyl, aryl, optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
m=1-12; and
n=1-12; or a pharmaceutically acceptable salt, or solvate thereof, wherein said compound inhibits neuronal damage.

7. The method according to claim 6, wherein the β-Amyloid induced disease is Alzheimer's disease or Down's syndrome.

8. The method of claim 1, wherein said cyclohexenone compound, or a pharmaceutically acceptable salt, or solvate thereof, is administered orally, parenterally or intravenously.

9. The method of claim 1, wherein said compound is isolated from *Antrodia camphorata*.

10. The method of claim 1, wherein R is a hydrogen, $C(=O)C_3H_8$, $C(=O)C_2H_5$, or $C(=O)CH_3$.

11. The method of claim 1, wherein each of $R_1$, $R_2$ and $R_3$ independently is a hydrogen, methyl, ethyl, propyl, butyl, pentyl, hexyl, heptyl, or octyl.

12. The method of any one of claim 11, wherein $R_1$ is hydrogen or methyl.

13. The method of any one of claim 11, wherein $R_2$ is a hydrogen or methyl.

14. The method of claim 1, wherein $R_4$ is $C_1$-$C_8$ alkyl optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

15. The method of claim 14, wherein $R_4$ is $CH_2CH{=}C(CH_3)_2$.

16. The method of claim 15, wherein said compound is

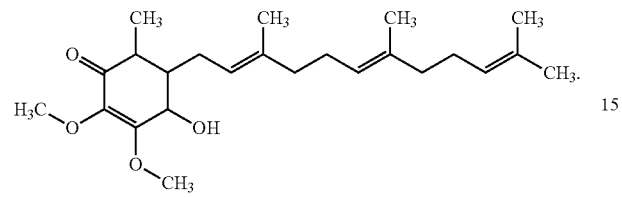

17. The method of claim 1, wherein said subject is human.

18. The method of claim 6, wherein said cyclohexenone compound, or a pharmaceutically acceptable salt, or solvate thereof, is administered orally, parenterally or intravenously.

* * * * *